(12) United States Patent
Sughrue et al.

(10) Patent No.: US 11,037,296 B1
(45) Date of Patent: Jun. 15, 2021

(54) DERIVING TARGET DATA FROM SELECTED BRAIN DATA

(71) Applicant: Omniscient Neurotechnology Pty Limited, Sydney (AU)

(72) Inventors: Michael Edward Sughrue, Sydney (AU); Stephane Philippe Doyen, Glebe (AU)

(73) Assignee: Omniscient Neurotechnology Pty Limited, Sydney (AU)

( * ) Notice: Subject to any disclaimer, the term of this patent is extended or adjusted under 35 U.S.C. 154(b) by 0 days.

(21) Appl. No.: 16/988,463

(22) Filed: Aug. 7, 2020

(51) Int. Cl.
| | |
|---|---|
| *G06K 9/00* | (2006.01) |
| *G06T 7/00* | (2017.01) |
| *G16H 50/50* | (2018.01) |
| *G16H 30/40* | (2018.01) |
| *G16H 20/70* | (2018.01) |
| *G16H 50/20* | (2018.01) |
| *G06T 7/11* | (2017.01) |
| *A61N 2/00* | (2006.01) |

(Continued)

(52) U.S. Cl.
CPC ............. *G06T 7/0016* (2013.01); *G06T 7/11* (2017.01); *G16H 20/70* (2018.01); *G16H 30/40* (2018.01); *G16H 50/20* (2018.01); *G16H 50/50* (2018.01); *A61N 2/006* (2013.01); *G01R 33/4806* (2013.01); *G01R 33/5608* (2013.01); *G06T 2207/10088* (2013.01); *G06T 2207/20128* (2013.01); *G06T 2207/30016* (2013.01)

(58) Field of Classification Search
CPC ...................... G06T 7/0016; G06T 7/11; G06T 2207/20128; G06T 2207/10088; G06T 2207/30016; G16H 20/70; G16H 30/40; G16H 50/20; G16H 50/50; G01R 33/5608; G01R 33/4806; A61N 2/006

See application file for complete search history.

(56) References Cited

U.S. PATENT DOCUMENTS 10,537,277 B2 * 1/2020 Wu .................... A61B 5/316
2016/0300352 A1 * 10/2016 Raj .................... G06T 7/0012

(Continued)

OTHER PUBLICATIONS

[No Author Listed], "Connectivity Matrices and Brain Graphs" Fundamentals of Brain Network Analysis, 2016, 89-113.

(Continued)

*Primary Examiner* — Tom Y Lu
(74) *Attorney, Agent, or Firm* — Fish & Richardson P.C.

(57) ABSTRACT

Methods, systems, and apparatus, including computer programs encoded on computer storage media, for determining a subset of brain data of a patient. One of the methods comprises providing connectivity data for presentation to a user, the connectivity data characterizing, for each pair of parcellations comprising a first parcellation and a second parcellation from a plurality of parcellations, a degree of correlation between the brain activity of the first parcellation and the brain activity of the second parcellation in the brain of a patient; determining one or more elements of interest in the connectivity data; determining one or more parcellations associated with elements of interest in the connectivity data; obtaining brain atlas data; determining a subset of the brain atlas data associated with the determined parcellations; and providing the subset of the brain atlas data to a user device for rendering the subset to the user.

20 Claims, 8 Drawing Sheets

(51) Int. Cl.
*G01R 33/48* (2006.01)
*G01R 33/56* (2006.01)

(56) References Cited

U.S. PATENT DOCUMENTS

| | | | | |
|---|---|---|---|---|
| 2018/0082169 | A1* | 3/2018 | Hahn | G16B 5/00 |
| 2018/0368720 | A1* | 12/2018 | Lee | G16H 50/20 |
| 2020/0170524 | A1* | 6/2020 | Assaf | A61B 5/4064 |
| 2020/0225308 | A1* | 7/2020 | Dosenbach | A61B 5/055 |
| 2021/0005306 | A1* | 1/2021 | Anticevic | A61B 5/7264 |

OTHER PUBLICATIONS

Becker et al., "Going Beyond Diffusion Tensor Imaging Tractography in Eloquent Glioma Surgery—High-Resolution Fiber Tractography: Q-Ball or Constrained Spherical Deconvolution?" World Neurosurg., Feb. 2020 134:e596-609.

Bonney et al., A Simplified Method of Accurate Postprocessing of Diffusion Tensor Imaging for Use in Brain Tumor Resection. Oper Neurosurg (Hagerstown) 13, 47-59 (2017).

Burks et al., "A method for safely resecting anterior butterfly gliomas: the surgical anatomy of the default mode network and the relevance of its preservation". J. Neurosurg., Sep. 2016, 126(6):1795-811.

Dell'Acqua and Tournier, "Modelling white matter with spherical deconvolution: How and why?" NMR Biomed., 2019, 32:e3945.

Faber et al., "Critical elements for connectivity analysis of brain networks" Universidade Federal de São Paulo—UNIFESP, 2019; 39 pages.

Fan et al., "The Human Brainnetome Atlas: A New Brain Atlas Based on Connectionl Architecture," Cereb Cortex, 2016, 26:3508-26.

Fischl, "FreeSurfer," Neuroimage, 2012, 62:774-81.

Garyfallidis et al., "Dipy, a library for the analysis of diffusion MRI data." Frontiers in Neuroinformatics, 2014, 8:1-17.

Glasser et al., "A multi-modal parcellation of human cerebral cortex," Nature, 2016, 536:171-8.

Glenn et al., "Common Disconnections in Glioma Surgery: An Anatomic Description," Cureus, 2017, 9:e1778.

Horwitz et al., "Interpreting the Effects of Altered Brain Anatomical Connectivityon fMRI Functional Connectivity: A Role for Computational NeuralModeling," Frontiers in Human Neurosci., Nov. 2013, 7:649.

Ille et al., Functional Reorganization of Cortical Language Function in Glioma Patients—A Preliminary Study. Frontiers in Oncology 9 (2019).

Jin et al., "Functional and anatomical connectivity-based parcellation of human cingulate cortex." Brain Behav., 2018, 8:e01070.

Ohue et al., "Evaluation of intraoperative brain shift using an ultrasound-linked navigation system for brain tumor surgery," Neurol. Med. Chir., 2010, 50:291-300.

Panesar et al., "Tractography for Surgical Neuro-Oncology Planning: Towards a Gold Standard," Neurotherapeutics, 2019, 16:36-51.

Rijnen et al., "Cognitive functioning in patients with low-grade glioma: effects of hemispheric tumor location and surgical procedure" 2019; 1(4):81-99.

Smitha et al., "Resting state fMRI: A review on methods in resting state connectivity analysis and resting state networks," Neuroradiol. J., 2017, 30:305-17.

* cited by examiner

DERIVING TARGET DATA FROM SELECTED BRAIN DATA

BACKGROUND

This specification relates to processing data related to the brain of a patient, e.g., functional magnetic resonance imaging (MM) data and/or tractography data.

Brain functional connectivity data characterizes, for each of one or more pairs of locations within the brain of a patient, the degree to which brain activity in the pair of locations is correlated.

One can gather data related to the brain of the patient by obtaining and processing images of the brain of the patient, e.g., using magnetic resonance imaging (MRI), diffusion tensor imaging (DTI), or functional MM imaging (fMRI). Diffusion tensor imaging uses magnetic resonance data to measure diffusion of water in a human brain. One can use the measured diffusion to generate tractography data, which can include images of neural tracts and corresponding white matter fibers of the subject brain.

Data related to the brain of a single patient can be highly complex and high-dimensional, and therefore difficult for a clinician to manually inspect and parse, e.g., to plan a surgery or diagnose the patient for a brain disease or mental disorder. For example, a correlation matrix, e.g., a correlation matrix of fMRI data, of the brain of a patient can be a matrix with hundreds of thousands or millions of elements.

SUMMARY

This specification relates to a system that can determine a subset of brain atlas data that is associated with a selected subset of brain data of a patient. The system can receive a user input identifying the selected subset of the brain data of the patient. The system can use the determined subset of the brain atlas data to generate target data for treatment of the patient. For example, the system can generate target data for high-precision targeted treatment of the brain, e.g., for transcranial magnetic stimulation (TMS). The system can also provide the subset of the brain atlas data for display to a user.

In this specification, brain data can be any data characterizing the brain of a patient. For example, brain data can include one or both of i) direct measurement data of the brain of the patient, e.g., images of the brain collected using brain imaging techniques, or ii) data that has been derived or generated from initial measurement data of the brain of the patient, e.g., correlation matrices.

In this specification, a parcellation is a predefined region of the brain. For example, a parcellation can be defined by boundaries on a three-dimensional volume of the brain. A parcellation can be defined such that the neurons in the parcellation are functionally similar according to one or more criteria. For example, a set of parcellations can be defined according to changes in cortical architecture, function, connectivity, and/or topography.

In this specification, a brain atlas is data that defines one or more parcellations of a brain of a patient, e.g., by defining the coordinates of the outline of the parcellation or the volume of the parcellation in a common three-dimensional coordinate system.

In this specification, target data can be any data that defines a particular region of the brain for targeted treatment. For example, target data can identify one or more particular parcellations of the brain of a patient, e.g., parcellations as defined by a brain atlas. In some cases, target data can be provided to one or more medical devices for executing the treatment of the patient, e.g., target data can be provided to an image guidance system for delivering treatment to the patient.

Particular embodiments of the subject matter described in this specification can be implemented so as to realize one or more of the following advantages.

As discussed above, a set of brain data characterizing the brain of a single patient can often be incredibly large and complicated, and thus it can be difficult and time consuming for a user to extract useful information from the set of brain data. Using techniques described in this specification, a system can quickly determine the subset of a brain atlas that is clinically relevant to a user and provide the determined subset for display to the user, so that the user is not forced to search through and analyze a large amount of data that is not clinically relevant. Therefore, the amount of time that a user must spend to discover the portion of the brain atlas that is useful to the user can be drastically reduced, resulting in improved outcomes for patients, users and/or clinicians, especially when effective care requires time sensitive investigations.

As a particular example, using existing systems it might take a user multiple hours to extract the subset of brain data of a patient required for a particular treatment, and because of the extensive time and attention required, the extracted subset can be inaccurate and error-prone. Using systems described in this specification, the process of extracting useful brain data from a corpus of brain data can be fully automated and executed in a matter of seconds or minutes.

In this specification, data is "clinically relevant" if the data represents an answer to a question that a trained clinician might ask in clinical practice treating patients, e.g., a question asked by a clinician in order to treat a patient with a specific disease. For example, clinically relevant data can be brain data characterizing a portion of the brain that a clinician has determined behaves anomalously.

Using some existing techniques, a user might only be able to generate target data that identifies a large portion of the brain of a patient, e.g., the frontal lobe. Using techniques described in this specification, a system can generate precise target data that can be used to execute highly personalized treatment of a patient. For example, a user can identify brain data that is anomalous, and the system can determine from the identified brain data a precise region (e.g., a single parcellation) in the brain of the patient that is behaving anomalously. The system can then generate target data for treating the determined region. Therefore, treatment can be highly targeted and personalized for individual patients, resulting in improved health outcomes for patients.

In this specification, a set of brain data is "anomalous" if the values of the brain data are outside a normal range of values, e.g., as defined by a data set that includes brain data corresponding to multiple other patients, e.g., multiple other patients not known to have anomalous brain data.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification describes a system that can generate target data for targeted treatment of the brain of a patient.

Figure 1A:
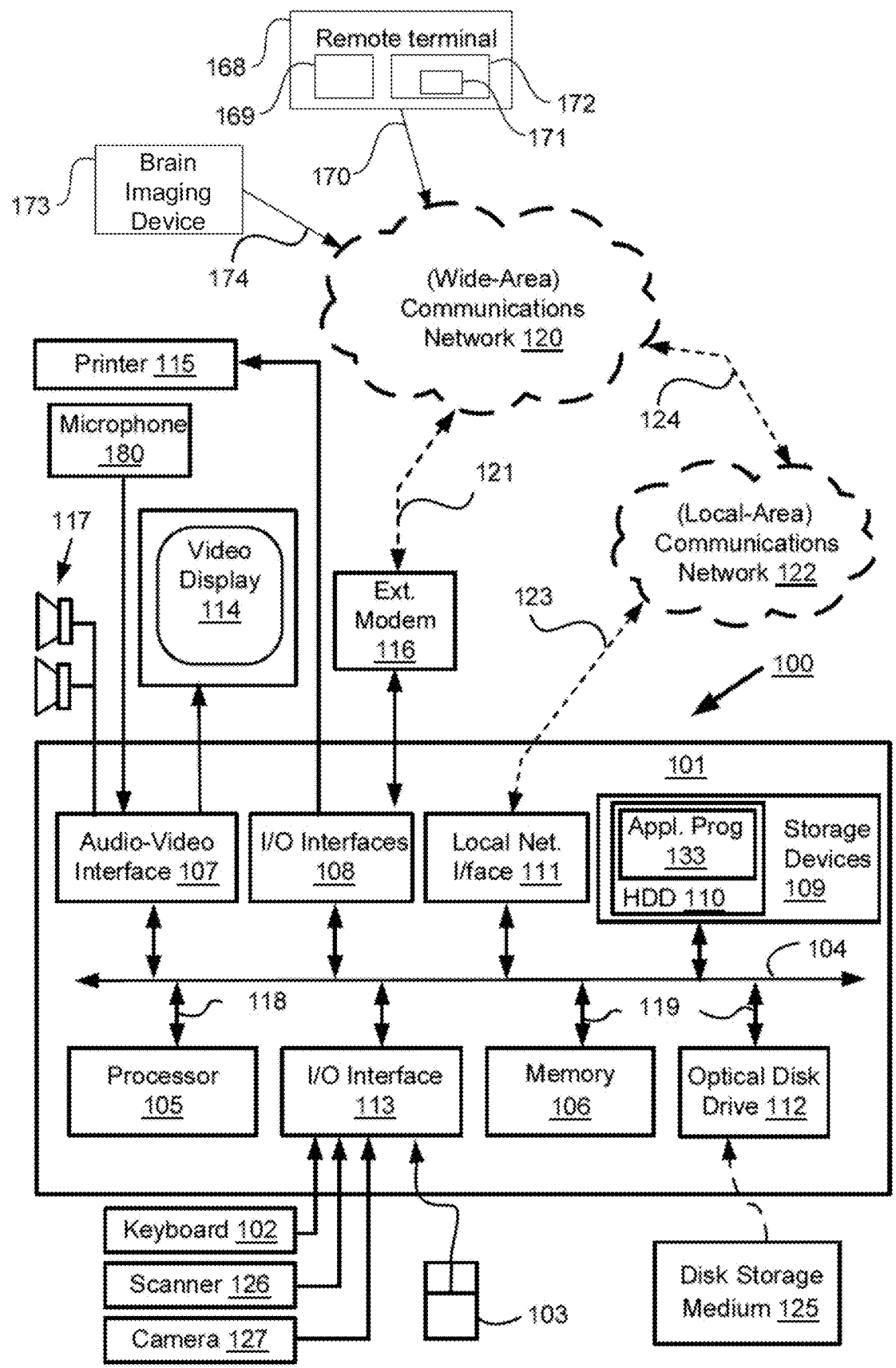
FIG. 1A and FIG. 1B are block diagrams that illustrate an example computer system for use in processing medical images.
Figure 1B:
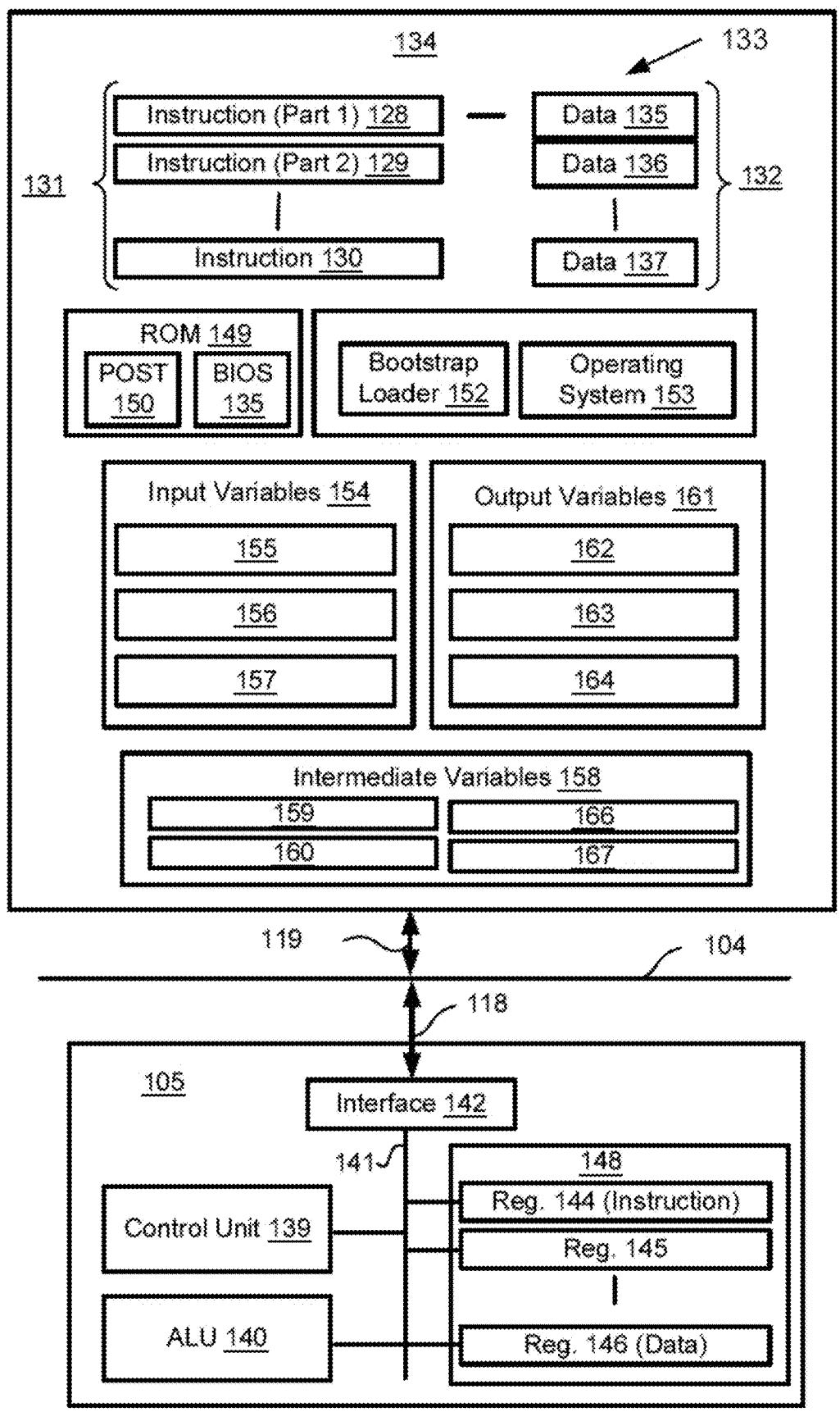

FIGS. 1A and 1B are block diagrams of a general-purpose computer system 100 upon which one can practice arrangements described in this specification. The following description is directed primarily to a computer server module 101. However, the description applies equally or equivalently to one or more remote terminals 168.

As seen in FIG. 1A, the computer system 100 includes: the server computer module 101; input devices such as a keyboard 102, a pointer device 103 (e.g., a mouse), a scanner 126, a camera 127, and a microphone 180; and output devices including a printer 115, a display device 114 and loudspeakers 117. An external Modulator-Demodulator (Modem) transceiver device 116 may be used by the computer server module 101 for communicating to and from the remote terminal 168 over a computer communications network 120 via a connection 121 and a connection 170. The aforementioned communication can take place between the remote terminal 168 and "the cloud" which in the present description comprises at least the one server module 101. The remote terminal 168 typically has input and output devices (not shown) which are similar to those described in regard to the server module 101. The communications network 120 may be a wide-area network (WAN), such as the Internet, a cellular telecommunications network, or a private WAN. Where the connection 121 is a telephone line, the modem 116 may be a traditional "dial-up" modem. Alternatively, where the connection 121 is a high capacity (e.g., cable) connection, the modem 116 may be a broadband modem. A wireless modem may also be used for wireless connection to the communications network 120.

The computer server module 101 typically includes at least one processor unit 105, and a memory unit 106. For example, the memory unit 106 may have semiconductor random access memory (RAM) and semiconductor read only memory (ROM). The remote terminal 168 typically includes as least one processor 169 and a memory 172. The computer server module 101 also includes a number of input/output (I/O) interfaces including: an audio-video interface 107 that couples to the video display 114, loudspeakers 117 and microphone 180; an I/O interface 113 that couples to the keyboard 102, mouse 103, scanner 126, camera 127 and optionally a joystick or other human interface device (not illustrated); and an interface 108 for the external modem 116 and printer 115. In some implementations, the modem 116 may be incorporated within the computer module 101, for example within the interface 108. The computer module 101 also has a local network interface 111, which permits coupling of the computer system 100 via a connection 123 to a local-area communications network 122, known as a Local Area Network (LAN). As illustrated in FIG. 1A, the local communications network 122 may also couple to the wide network 120 via a connection 124, which would typically include a so-called "firewall" device or device of similar functionality. The local network interface 111 may include an Ethernet circuit card, a Bluetooth® wireless arrangement or an IEEE 802.11 wireless arrangement; however, numerous other types of interfaces may be practiced for the interface 111.

The I/O interfaces 108 and 113 may afford either or both of serial or parallel connectivity; the former may be implemented according to the Universal Serial Bus (USB) standards and having corresponding USB connectors (not illustrated). Storage memory devices 109 are provided and typically include a hard disk drive (HDD) 110. Other storage devices such as a floppy disk drive and a magnetic tape drive (not illustrated) may also be used. An optical disk drive 112 is typically provided to act as a non-volatile source of data. Portable memory devices, such optical disks (e.g., CD-ROM, DVD, Blu-ray Disc™), USB-RAM, portable, external hard drives, and floppy disks, for example, may be used as appropriate sources of data to the system 100.

The components 105 to 113 of the computer module 101 typically communicate via an interconnected bus 104 and in a manner that results in a conventional mode of operation of the computer system 100 known to those in the relevant art. For example, the processor 105 is coupled to the system bus 104 using a connection 118. Likewise, the memory 106 and optical disk drive 112 are coupled to the system bus 104 by connections 119.

The techniques described in this specification may be implemented using the computer system 100, e.g., may be implemented as one or more software application programs 133 executable within the computer system 100. In some implementations, the one or more software application programs 133 execute on the computer server module 101 (the remote terminal 168 may also perform processing jointly with the computer server module 101), and a browser 171 executes on the processor 169 in the remote terminal, thereby enabling a user of the remote terminal 168 to access the software application programs 133 executing on the server 101 (which is often referred to as "the cloud") using the browser 171. In particular, the techniques described in this specification may be effected by instructions 131 (see FIG. 1B) in the software 133 that are carried out within the computer system 100. The software instructions 131 may be formed as one or more code modules, each for performing one or more particular tasks. The software may also be divided into two separate parts, in which a first part and the corresponding code modules performs the described techniques and a second part and the corresponding code modules manage a user interface between the first part and the user.

The software may be stored in a computer readable medium, including the storage devices described below, for example. The software is loaded into the computer system 100 from the computer readable medium, and then executed by the computer system 100. A computer readable medium having such software or computer program recorded on the computer readable medium is a computer program product. Software modules for that execute techniques described in this specification may also be distributed using a Web browser.

The software 133 is typically stored in the HDD 110 or the memory 106 (and possibly at least to some extent in the memory 172 of the remote terminal 168). The software is loaded into the computer system 100 from a computer readable medium, and executed by the computer system 100. Thus, for example, the software 133, which can include one or more programs, may be stored on an optically readable disk storage medium (e.g., CD-ROM) 125 that is read by the optical disk drive 112. A computer readable medium having such software or computer program recorded on it is a computer program product.

In some instances, the application programs 133 may be supplied to the user encoded on one or more CD-ROMs 125 and read via the corresponding drive 112, or alternatively may be read by the user from the networks 120 or 122. Still further, the software can also be loaded into the computer system 100 from other computer readable media. Computer readable storage media refers to any non-transitory tangible storage medium that provides recorded instructions and/or data to the computer system 100 for execution and/or processing. Examples of such storage media include floppy disks, magnetic tape, CD-ROM, DVD, Blu-ray™ Disc, a hard disk drive, a ROM or integrated circuit, USB memory, a magneto-optical disk, or a computer readable card such as a PCMCIA card and the like, whether or not such devices are internal or external of the computer module 101. Examples of transitory or non-tangible computer readable transmission media that may also participate in the provision of software, application programs, instructions and/or data to the computer module 101 include radio or infra-red transmission channels as well as a network connection to another computer or networked device, and the Internet or Intranets including e-mail transmissions and information recorded on Websites and the like.

The second part of the application programs 133 and the corresponding code modules mentioned above may be executed to implement one or more graphical user interfaces (GUIs) to be rendered or otherwise represented upon the display 114. For example, through manipulation of the keyboard 102 and the mouse 103, a user of the computer system 100 and the application may manipulate the interface in a functionally adaptable manner to provide controlling commands and/or input to the applications associated with the GUI(s). Other forms of functionally adaptable user interfaces may also be implemented, such as an audio interface utilizing speech prompts output via the loudspeakers 117 and user voice commands input via the microphone 180.

FIG. 1B is a detailed schematic block diagram of the processor 105 and a "memory" 134. The memory 134 represents a logical aggregation of all the memory modules (including the HDD 109 and semiconductor memory 106) that can be accessed by the computer module 101 in FIG. 1A.

When the computer module 101 is initially powered up, a power-on self-test (POST) program 150 can execute. The POST program 150 can be stored in a ROM 149 of the semiconductor memory 106 of FIG. 1A. A hardware device such as the ROM 149 storing software is sometimes referred to as firmware. The POST program 150 examines hardware within the computer module 101 to ensure proper functioning and typically checks the processor 105, the memory 134 (109, 106), and a basic input-output systems software (BIOS) module 151, also typically stored in the ROM 149, for correct operation. Once the POST program 150 has run successfully, the BIOS 151 can activate the hard disk drive 110 of FIG. 1A. Activation of the hard disk drive 110 causes a bootstrap loader program 152 that is resident on the hard disk drive 110 to execute via the processor 105. This loads an operating system 153 into the RAM memory 106, upon which the operating system 153 commences operation. The operating system 153 is a system level application, executable by the processor 105, to fulfil various high-level functions, including processor management, memory management, device management, storage management, software application interface, and generic user interface.

The operating system 153 manages the memory 134 (109, 106) to ensure that each process or application running on the computer module 101 has sufficient memory in which to execute without colliding with memory allocated to another process. Furthermore, the different types of memory available in the system 100 of FIG. 1A must be used properly so that each process can run effectively. Accordingly, the aggregated memory 134 is not intended to illustrate how particular segments of memory are allocated (unless otherwise stated), but rather to provide a general view of the memory accessible by the computer system 100 and how such is used.

As shown in FIG. 1B, the processor 105 includes a number of functional modules including a control unit 139, an arithmetic logic unit (ALU) 140, and a local or internal memory 148, sometimes called a cache memory. The cache memory 148 typically includes a number of storage registers 144-146 in a register section. One or more internal busses 141 functionally interconnect these functional modules. The processor 105 typically also has one or more interfaces 142 for communicating with external devices via the system bus 104, using a connection 118. The memory 134 is coupled to the bus 104 using a connection 119.

The application program 133 includes a sequence of instructions 131 that may include conditional branch and loop instructions. The program 133 may also include data 132 which is used in execution of the program 133. The instructions 131 and the data 132 are stored in memory locations 128, 129, 130 and 135, 136, 137, respectively. Depending upon the relative size of the instructions 131 and the memory locations 128-130, a particular instruction may be stored in a single memory location as depicted by the instruction shown in the memory location 130. Alternately, an instruction may be segmented into a number of parts each of which is stored in a separate memory location, as depicted by the instruction segments shown in the memory locations 128 and 129.

In general, the processor 105 is given a set of instructions which are executed therein. The processor 105 waits for a subsequent input, to which the processor 105 reacts to by executing another set of instructions. Each input may be provided from one or more of a number of sources, including data generated by one or more of the input devices 102, 103, data received from an external source 173, e.g., a brain imaging device 173 such such as an MRI or DTI scanner, across one of the networks 120, 122, data retrieved from one of the storage devices 106, 109 or data retrieved from a storage medium 125 inserted into the corresponding reader 112, all depicted in FIG. 1A. The execution of a set of the instructions may in some cases result in output of data. Execution may also involve storing data or variables to the memory 134.

Some techniques described in this specification use input variables 154, e.g., data sets characterizing the brain of a patient, which are stored in the memory 134 in corresponding memory locations 155, 156, 157. The techniques can produce output variables 161, which are stored in the memory 134 in corresponding memory locations 162, 163, 164. Intermediate variables 158 may be stored in memory locations 159, 160, 166 and 167.

Referring to the processor 105 of FIG. 1B, the registers 144, 145, 146, the arithmetic logic unit (ALU) 140, and the control unit 139 work together to perform sequences of micro-operations needed to perform "fetch, decode, and execute" cycles for every instruction in the instruction set making up the program 133. Each fetch, decode, and execute cycle can include i) a fetch operation, which fetches or reads an instruction 131 from a memory location 128, 129, 130; ii) a decode operation in which the control unit 139 determines which instruction has been fetched; and iii) an execute operation in which the control unit 139 and/or the ALU 140 execute the instruction.

Thereafter, a further fetch, decode, and execute cycle for the next instruction may be executed. Similarly, a store cycle may be performed by which the control unit 139 stores or writes a value to a memory location 132.

Each step or sub-process in the techniques described in this specification may be associated with one or more segments of the program 133 and is performed by the register section 144, 145, 146, the ALU 140, and the control unit 139 in the processor 105 working together to perform the fetch, decode, and execute cycles for every instruction in the instruction set for the noted segments of the program 133. Although a cloud-based platform has been described for practicing the techniques described in this specification, other platform configurations can also be used. Furthermore, other hardware/software configurations and distributions can also be used for practicing the techniques described in this specification.

Figure 2A:
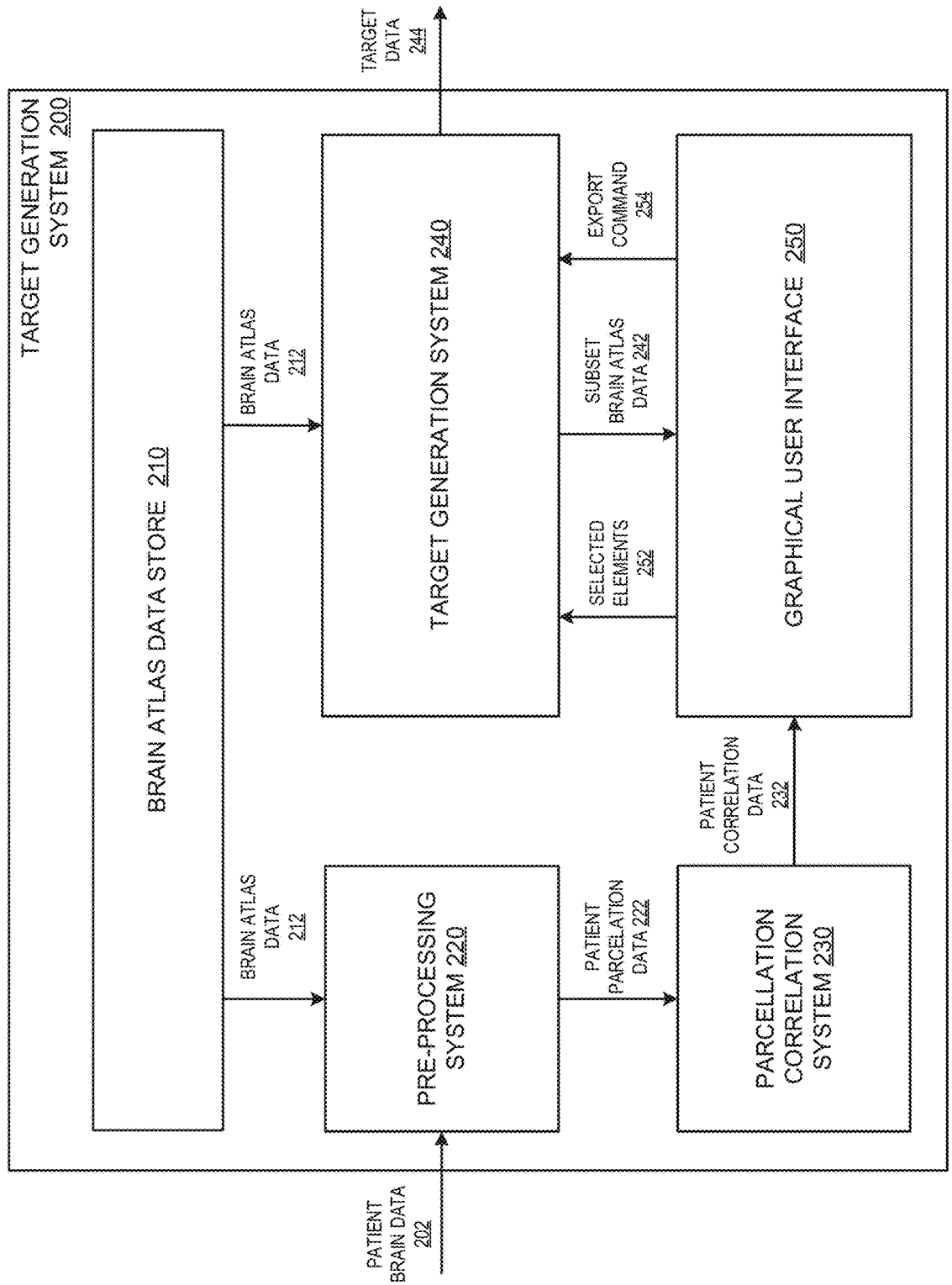
FIG. 2A and FIG. 2B are diagrams of an example target generation system.
Figure 2B:
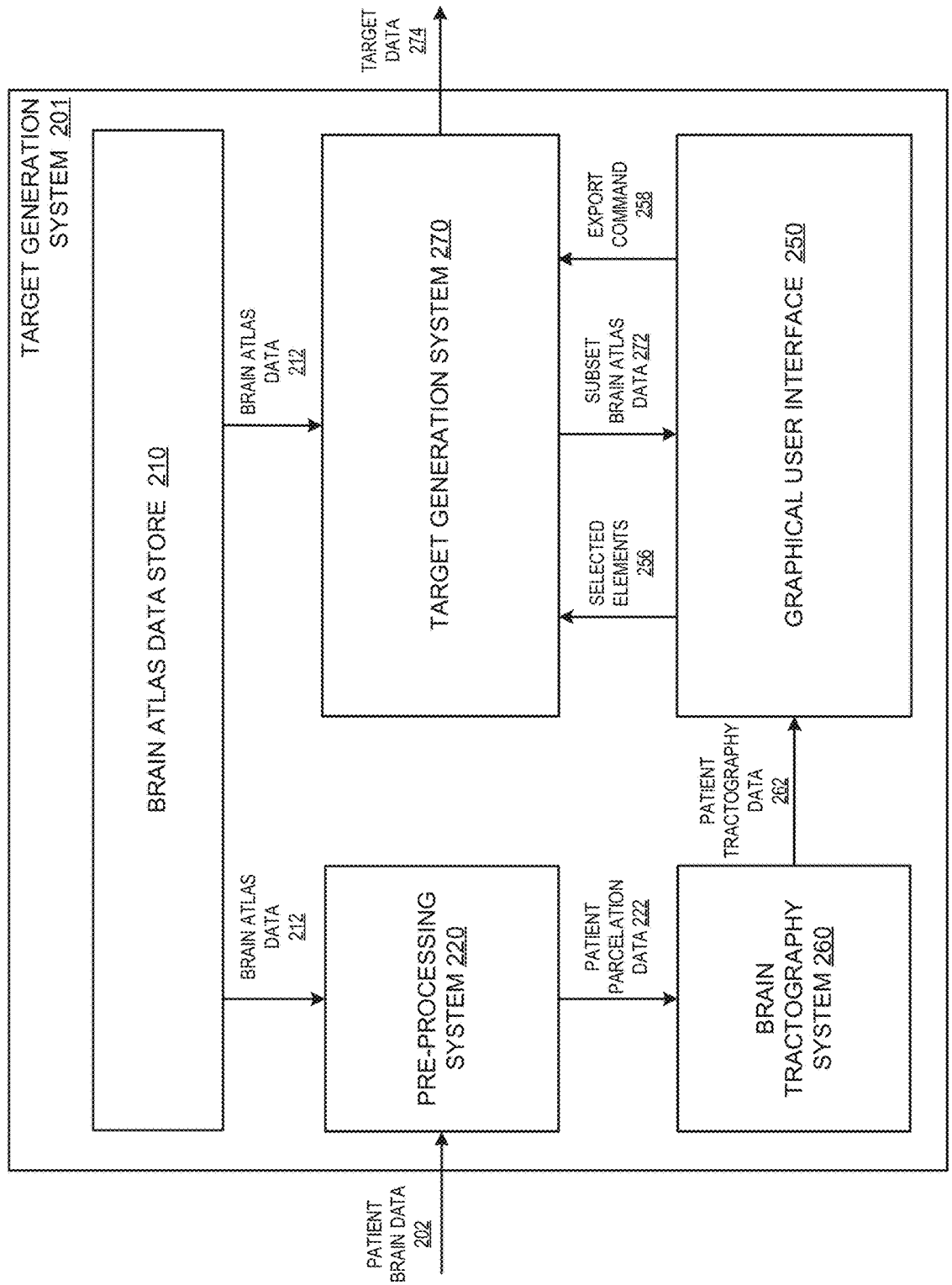

FIGS. 2A and 2B are diagrams of example target generation systems 200 and 201, respectively. The target generation systems 200 and 201 are examples of systems implemented as computer programs on one or more computers in one or more locations, in which the systems, components, and techniques described below can be implemented. As depicted in FIG. 2A, the target generation system 200 is configured to determine a subset of brain atlas data according to a user selection of one or more particular elements of patent correlation data. As depicted in FIG. 2B, the target generation system 200 is configured to determine a subset of brain atlas data according to a user selection of one or more particular elements of patient tractography data.

Referring to FIG. 2A, the target generation system 200 is configured to obtain patient brain data 202 characterizing the brain of a patient and process the patient brain data 202 to generate target data 244. For example, the patient brain data 202 can include one or more of blood-oxygen-level-dependent imaging data, fMRI data, or EEG data captured from the brain of the patient.

The target generation system 200 includes a brain atlas data store 210, a pre-processing system 220, a parcellation correlation system 230, a target generation system 240, and a graphical user interface 250.

In some implementations, the target generation system 200 is local to the user, e.g., a component of a user device. In some other implementations, one or more components of the target generation system 200 are non-local to the user, e.g., hosted within a data center, which can be a distributed computing system having hundreds or thousands of computers in one or more locations. As a particular example, the graphical user interface 250 might be local to the user, while each of the other components of the target generation system 200 are on the cloud and communicatively connected to the graphical user interface 250.

The brain atlas data store 210 is configured to maintain brain atlas data 212, which defines multiple parcellations of the human brain. For example, the brain atlas data 212 can include a model of the brain composed of three-dimensional voxels, where each voxel is defined by a location and orientation in a common coordinate system of the brain. Each voxel can be assigned to a particular parcellation, so that the location and shape of each parcellation is defined by the respective voxels assigned to the parcellation. As a particular example, the brain atlas data 212 can be stored using a tabular format that maps (x,y,z) locations within the brain to an identification of a particular parcellation. As another particular example, the brain atlas data 212 can be stored in a document-oriented database, e.g., using a JSON model. As another particular example, the brain atlas data 212 can be stored using a collection of three-dimensional tensors that identify, for respective (x,y,z) locations within the brain, a particular parcellation.

The pre-processing system 220 is configured to obtain the patient brain data 202 and process the patient brain data 202 to generate patient parcellation data 222 which organizes the patient brain data 202 according to multiple different parcellations of the brain of the patient. The pre-processing system 220 can generate the patient parcellation data 222 according to the brain atlas data 212, obtained from the brain atlas data store 210. For example, the patient brain data 202 can include multiple different time series characterizing the activity of a respective different region of the brain of the patient over time, e.g., a respective time series corresponding to each three-dimensional voxel of the brain that can be measured by an MRI machine. The pre-processing system 220 can organize the different time series signals by parcellation according to a brain atlas of the brain. For example, for each voxel in the brain data 202, the pre-processing system 220 can determine the parcellation to which the corresponding voxel in the brain atlas data 212 is assigned. The pre-processing system 220 can then, for each parcellation, combine the different time series signals corresponding to the parcellation, e.g., by determining an average of the different time series signals.

In some implementations the pre-processing system 220 performs one or more additional pre-processing steps to generate the patient parcellation data 222. For example, the pre-processing system 220 can perform smoothing on the patient brain data 202, e.g., to remove components of the patient brain data 202 that are not clinically relevant such as brain activity data related to the heartbeat or breathing of the patient. As another example, the pre-processing system 220 can perform skull stripping on the patient brain data 202. As another example, the pre-processing system 220 can remove one or more slices in brain data 202 in order to allow for signal stabilization. As another example, the pre-processing system 220 can perform slice timing correction on the brain data 202. As another example, the pre-processing system 220 can perform motion correction on the brain data 202. As another example, the pre-processing system 220 can perform gradient distortion correction on the brain data 202. As another example, the pre-processing system 220 can perform global intensity normalization on the brain data 202. As another example, the pre-processing system 220 can calculate one or more confounds using the brain data 202. As another example, the pre-processing system 220 can apply a whitening transform to the brain data 202.

The parcellation correlation system 230 is configured to obtain the patient parcellation data 222 and to process the patient parcellation data 222 to generate patient correlation data 232 that characterizes, for each pair of parcellations of the multiple parcellations in the patient parcellation data 222, a correlation between brain activity of the first parcellation and brain activity of the second parcellation in the brain of the patient.

For example, the patient parcellation data 222 can include one or more time series signals corresponding to each parcellation, and the parcellation correlation system 230 can determine, for each pair of parcellations, a correlation between the values of the time series of the first parcellation and the time series of the second parcellation.

In some implementations, the parcellation correlation system 230 processes the patient parcellation data to generate a correlation matrix for display to the user. A correlation matrix can be generated from the brain functional connectivity data of a patient, and displays the correlation between areas of the brain of the patient. In particular, for an element of a correlation matrix in a row that corresponds to a first parcellation of the brain and in a column that corresponds to a second parcellation of the brain, the value of the element characterizes the correlation between the first parcellation and the second parcellation.

In some implementations, the parcellation correlation system 230 determines one or more pairs of parcellations whose correlation is anomalous. For example, the parcellation correlation system 230 can obtain normal correlation data that identifies, for each pair of parcellations in the patient parcellation data 222, a range of values for the correlation between the pair of parcellations that is considered "normal." The normal range can be determined according to the correlation between the pair of parcellations measured in the respective brain of multiple other patients. For example, the normal correlation data can be determined from brain data captured from hundreds, thousands, or millions of other patients. As a particular example, the normal correlation data might identify, for each pair of parcellations, an average correlation between the pair of parcellations and a standard deviation of correlations between the pair of parcellations, as determined from the correlations measured in the brains of the other patients. Using the normal correlation data, the parcellation correlation system 230 can determine one or more pairs of parcellations in the patient parcellation data 222 whose correlation is anomalous, and identify the one or more determined pairs of parcellations in the patient correlation data 232.

In some implementations, the parcellation correlation system 230 generates an anomaly correlation matrix for display to the user. In this specification, an anomaly correlation matrix is a correlation matrix that visually identifies one or more pairs of parcellations, corresponding to respective elements in the anomaly correlation matrix, whose correlation has been determined to be anomalous. Correlation matrices and anomaly correlation matrices are discussed in more detail below with respect to FIG. 3.

The graphical user interface 250 is configured to obtain the patient correlation data 232 and display data characterizing the patient correlation data 232 to the user. For example, the graphical user interface 250 can display a list of the correlation between each pair of parcellations. As another example, the graphical user interface 250 can display a list of one or more pairs of parcellations whose correlation the parcellation correlation system 230 has determined to be anomalous. As another example, the graphical user interface 250 can display a correlation matrix or anomaly correlation matrix characterizing the correlation between respective pairs of parcellations in the brain of the patient. As another example, the graphical user interface 250 can display a text summary of the pairs of parcellations whose correlation the parcellation correlation system 230 has determined to be anomalous. As another example, the graphical user interface 250 can display a score calculated by the parcellation correlation system 230 that characterizes a degree of anomaly in the brain of the patient, e.g., a value between 0 and 1.

In some implementations, the graphical user interface 250 can also display one or more components of the patient brain data 202 to the user. For example, the graphical user interface 250 might display brain image data, e.g, MRI images of the brain of the user.

The graphical user interface 250 is configured to receive a user input identifying one or more particular elements 252 of the patient correlation data. The selected elements 252 can include any subset of the patient correlation data 232. For example, the selected elements 252 of the patient correlation data can include a particular pair of parcellations, a particular parcellation, a group of pairs of parcellations, and/or a group of parcellations (e.g., each parcellation associated with the language region of the brain). The user can select the one or more particular elements 252 using any appropriate user input device, e.g., the pointer device 103, or the microphone 180 depicted in FIG. 1A. As a particular example, the user can select a particular row or column of the correlation matrix or the anomaly correlation matrix. This process is discussed in more detail below with respect to FIG. 4A and FIG. 4B.

The graphical user interface 250 can provide the selected elements 252 to the target generation system 240. The target generation system 240 is configured to process the selected elements 252 to determine a set of one or more particular parcellations associated with the selected elements 252. For example, if the selected elements 252 identify one or more pairs of parcellations, the target generation system 240 can determine the set of parcellations to include each parcellation included in the one or more pairs of parcellations.

The target generation system 240 can obtain the brain atlas data 212 from the brain atlas data store 210, and use the brain atlas data 212 to generate a subset 242 of the brain atlas data that corresponds to the determined set of parcellations. That is, the determined subset 242 of the brain atlas data characterizes the location and shape of the parcellations in the determined set of parcellations. For example, the subset 242 of brain atlas data can identify each three-dimensional voxel in the brain atlas data 212 that is assigned to a parcellation in the determined set of parcellations.

The graphical user interface 250 can receive the subset 242 of the brain atlas data and render the subset 242 for the user. For example, the graphical user interface 250 can display a three-dimensional model of the parcellations characterized by the subset 242 of the brain atlas data. That is, the graphical user interface 250 can display to the user a model of the parcellations corresponding to the elements 252 that were selected by the user. This process is discussed in more detail below with respect to FIG. 4A and FIG. 4B.

The graphical user interface 250 can receive a user input characterizing an export command 254 to export the subset 242 of the brain atlas data. The user can provide the export command 254 using any appropriate user input device, e.g., the pointer device 103, or the microphone 180 depicted in FIG. 1A. The graphical user interface 250 can then provide the export command 254 to the target generation system 240.

In response to receiving the export command 254, the target generation system 240 can generate target data 244 that characterizes the subset 242 of the brain atlas data. The target generation system 240 can then export the target data 244 to an external system. For example, the target generation system 240 can provide the target data 244 to an external device for delivering a treatment to the patient, e.g., an image guidance system for delivering a TMS treatment to the patient. As another example, the target generation system 240 can provide the target data 244 to an external guidance device to be used during targeted surgery of the patient. As another example, the target generation system 240 can provide the target data 244 to an external user system for further analysis by the user. As another example, the target generation system 240 can provide the target data 244 to an external machine learning system to be used as an input to one or more machine learning models.

In some implementations, the target generation system 240 generates and exports the target data 244 when the target generation system 240 receives the selected elements 252. That is, the export command 254 can be included in the data sent to the target generation system 240 characterizing the selected elements 252, so that the target generation system 240 does not send the subset 242 of the brain atlas data 242 to the graphical user interface 250 for display to the user, but rather immediately generates and exports the target data 244.

Referring to FIG. 2B, the target generation system 201 is configured to obtain patient brain data 202 characterizing the brain of a patient and process the patient brain data 202 to generate target data 274. For example, the patient brain data 202 can include one or more of blood-oxygen-level-dependent imaging data, fMRI data, or EEG data captured from the brain of the patient.

The target generation system 200 includes a brain atlas data store 210, a pre-processing system 220, a brain tractography system 260, a target generation system 270, and a graphical user interface 250.

As described above with reference to FIG. 2A, in some implementations, the target generation system 201 is local to the user, e.g., a component of a user device. In some other implementations, one or more components of the target generation system 200 are non-local to the user, e.g., hosted within a data center, which can be a distributed computing system having hundreds or thousands of computers in one or more locations.

The brain atlas data store 210 is configured to maintain brain atlas data 212, which defines multiple parcellations of the human brain.

The pre-processing system 220 is configured to obtain the patient brain data 202 and process the patient brain data 202 to generate patient parcellation data 222 which organizes the patient brain data 202 according to multiple different parcellations of the brain of the patient. The pre-processing system 220 can generate the patient parcellation data 222 according to the brain atlas data 212, obtained from the brain atlas data store 210. As described above with reference to FIG. 2A, in some implementations the pre-processing system 220 performs one or more additional pre-processing steps to generate the patient parcellation data 222.

The brain tractography system 260 is configured to obtain the patient parcellation data 222 and to process the patient parcellation data 222 to generate patient tractography data 262 that characterizes, for each pair of parcellations of multiple parcellations in the patient parcellation data 222, neural tracts connecting the pair of parcellations in the brain of the patient.

In some implementations, the brain tractography system 260 determines one or more pairs of parcellations for which the number of connections in the patient tractography data 262 is anomalous. For example, the brain tractography system 260 can obtain normal tractography data that identifies, for each pair of parcellations in the patient parcellation data 222, a range of values for the number of tracts connecting the pair of parcellations that is considered "normal." The normal range can be determined according to the number of tracts connecting the pair of parcellations measured in the respective brains of multiple other patients. For example, the normal tractography data can be determined from brain data captured from hundreds, thousands, or millions of other patients. As a particular example, the normal tractography data might identify, for each pair of parcellations, an average number of tracts between the pair of parcellations and a standard deviation of the number of tracts between the pair of parcellations, as determined from the neural tracts measured in the brains of the other patients. Using the normal tractography data, the brain tractography system 260 can determine one or more pairs of parcellations in the patient parcellation data 222 for which the number of tracts connecting the pair of parcellations is anomalous, and identify the one or more determined pairs of parcellations in the patient tractography data 262.

The graphical user interface 250 is configured to obtain the patient tractography data 262 and display data characterizing the patient tractography data 262 to the user. For example, the graphical user interface 250 can display a list of the number of tracts between each pair of parcellations. As another example, the graphical user interface 250 can display a list of one or more pairs of parcellations whose number of connecting tracts the brain tractography system 260 has determined to be anomalous. As another example, the graphical user interface 250 can display a matrix characterizing the number of tracts connecting respective pairs of parcellations in the brain of the patient. As another example, the graphical user interface 250 can display a text summary of the pairs of parcellations whose number of connecting tracts the brain tractography system 260 has determined to be anomalous. As another example, the graphical user interface 250 can display a score calculated by the tractography system 260 that characterizes a degree of anomaly in the brain of the patient, e.g., a value between 0 and 1.

In some implementations, the graphical user interface 250 can also display one or more components of the patient brain data 202 to the user. For example, the graphical user interface 250 might display brain image data, e.g, MRI images of the brain of the user.

The graphical user interface 250 is configured to receive a user input identifying one or more particular elements 256 of the patient tractography data 262. The selected elements 256 can include any subset of the patient tractography data 262. For example, the selected elements 256 of the patient tractography data 262 can include a particular pair of parcellations, a particular parcellation, a group of pairs of parcellations, and/or a group of parcellations (e.g., each parcellation associated with the language region of the brain).

The graphical user interface 250 can provide the selected elements 256 to the target generation system 270. The target generation system 270 is configured to process the selected elements 256 to determine a set of one or more particular parcellations associated with the selected elements 256. For example, if the selected elements 256 identify one or more pairs of parcellations, the target generation system 270 can determine the set of parcellations to include each parcellation included in the one or more pairs of parcellations.

The target generation system 270 can obtain the brain atlas data 212 from the brain atlas data store 210, and use the brain atlas data 212 to generate a subset 272 of the brain atlas data that corresponds to the determined set of parcellations. That is, the determined subset 272 of the brain atlas data characterizes the location and shape of the parcellations in the determined set of parcellations. For example, the subset 272 of brain atlas data can identify each three-dimensional voxel in the brain atlas data 212 that is assigned to a parcellation in the determined set of parcellations.

The graphical user interface 250 can receive the subset 272 of the brain atlas data and render the subset 272 for the user. For example, the graphical user interface 250 can display a three-dimensional model of the parcellations characterized by the subset 272 of the brain atlas data. That is, the graphical user interface 250 can display to the user a model of the parcellations corresponding to the elements 256 that were selected by the user. This process is discussed in more detail below with respect to FIG. 4A and FIG. 4B.

The graphical user interface 250 can receive a user input characterizing an export command 258 to export the subset 272 of the brain atlas data. The graphical user interface 250 can then provide the export command 258 to the target generation system 270.

In response to receiving the export command 258, the target generation system 270 can generate target data 274 that characterizes the subset 272 of the brain atlas data. The target generation system 270 can then export the target data 274 to an external system, as described above with reference to FIG. 2A.

In some implementations, the target generation system 270 generates and exports the target data 274 when the target generation system 270 receives the selected elements 256. That is, the export command 258 can be included in the data sent to the target generation system 270 characterizing the selected elements 256, so that the target generation system 270 does not send the subset 272 of the brain atlas data 272 to the graphical user interface 250 for display to the user, but rather immediately generates and exports the target data 274.

Figure 3:
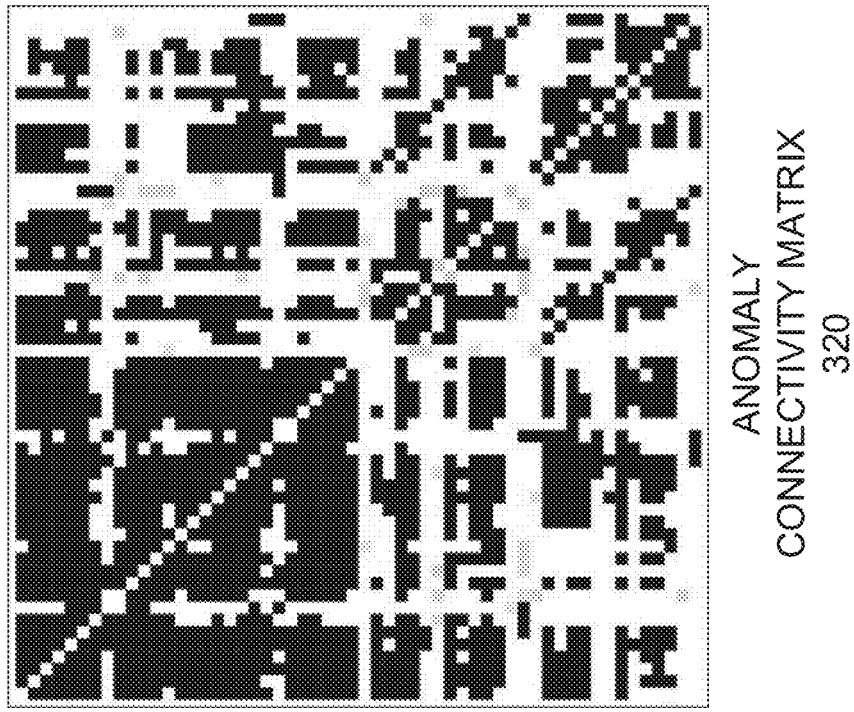
FIG. 3 illustrates an example connectivity matrix and an example anomaly connectivity matrix.
Figure 3:
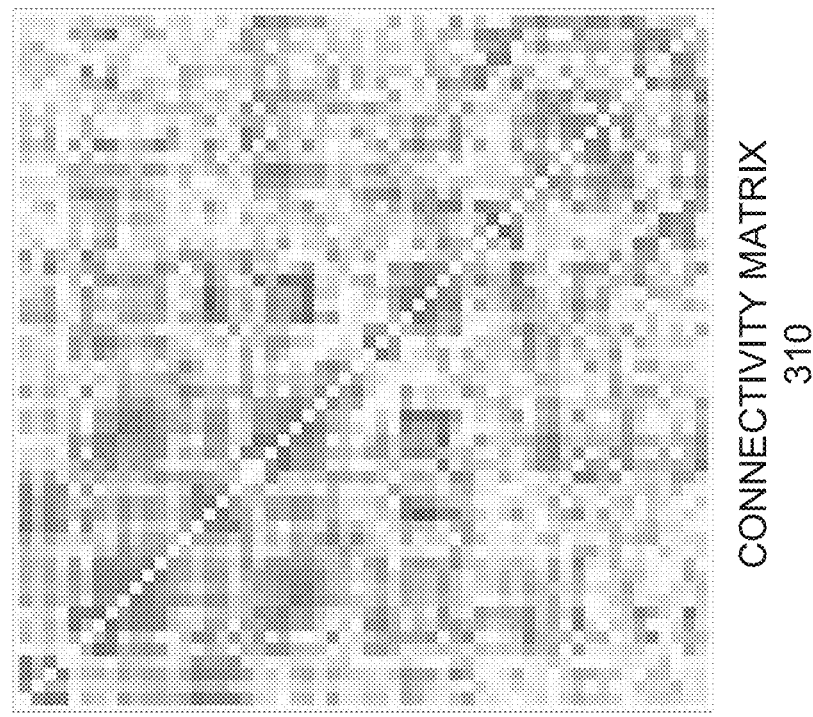

FIG. 3 is an illustration of an example connectivity matrix 310 and an example anomaly connectivity matrix 320.

The connectivity matrix 310 identifies, for each pair of parcellations of multiple parcellations in the brain of a patient, the correlation between brain activity of the first parcellation of the pair of parcellations and the brain activity of the second parcellation of the pair of parcellations. That is, each row and column of the connectivity matrix 310 corresponds to a parcellation, and each element has a value identifying the correlation between the parcellation corresponding to the row of the element and the parcellation corresponding to the column of the element. In some implementations, the connectivity matrix 310 can include ranges of two different colors, where the first color corresponds to negative correlations and the second color corresponds to positive correlations, and the intensity of a color corresponds to a magnitude of the negative or positive correlation. The anomaly connectivity matrix 320 visually identifies one or more pairs of parcellations whose correlation is anomalous. In particular, the anomaly matrix 320 visually identifies elements that correspond to pairs of parcellations whose correlations have been determined to be too variable (in black), elements that correspond to pairs of parcellations whose correlations have been determined to be "normal" (in white), and elements that correspond to pairs of parcellations whose correlations have been determined to be anomalous (in grayscale).

Anomaly correlation matrices are discussed in more detail in U.S. patent application Ser. No. 16/920,078, the entire contents of which are hereby incorporated by reference.

Figure 4A:
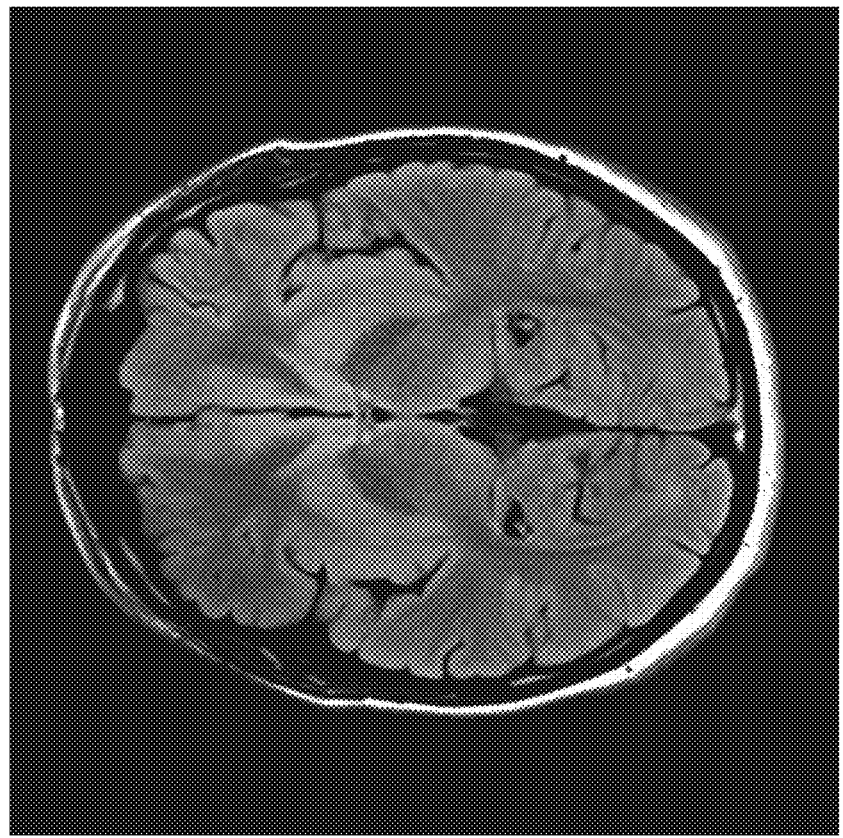
FIG. 4A illustrates an example connectivity matrix and corresponding brain image data.
Figure 4A:
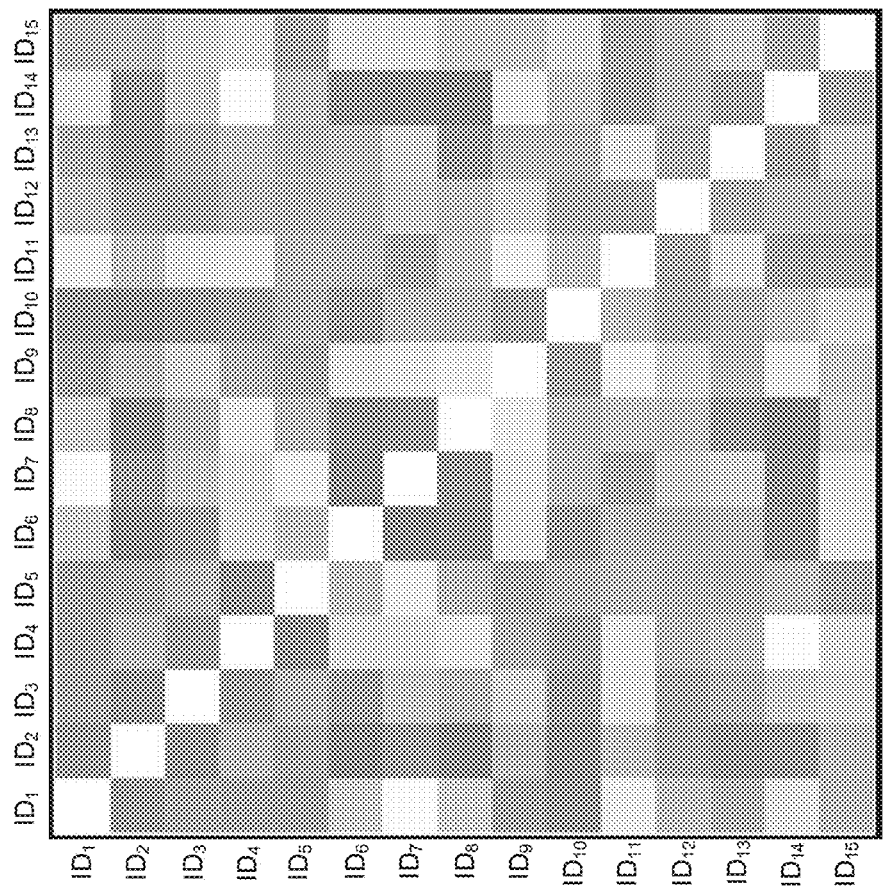

FIG. 4A illustrates an example connectivity matrix 410 and corresponding brain image data 420. Although a standard connectivity matrix is depicted in FIG. 4A, it is to be understood that the following description can also apply to anomaly connectivity matrices.

The connectivity matrix 410 and brain image data 420 can be displayed to a user by a graphical user interface, e.g., the graphical user interface 250 depicted in FIG. 2. The graphical user interface can allow the user to select one or more rows or columns of the connectivity matrix 410. Because the user has not yet selected a row or column, the entire brain of the patient can be depicted in the brain image data 420.

Figure 4B:
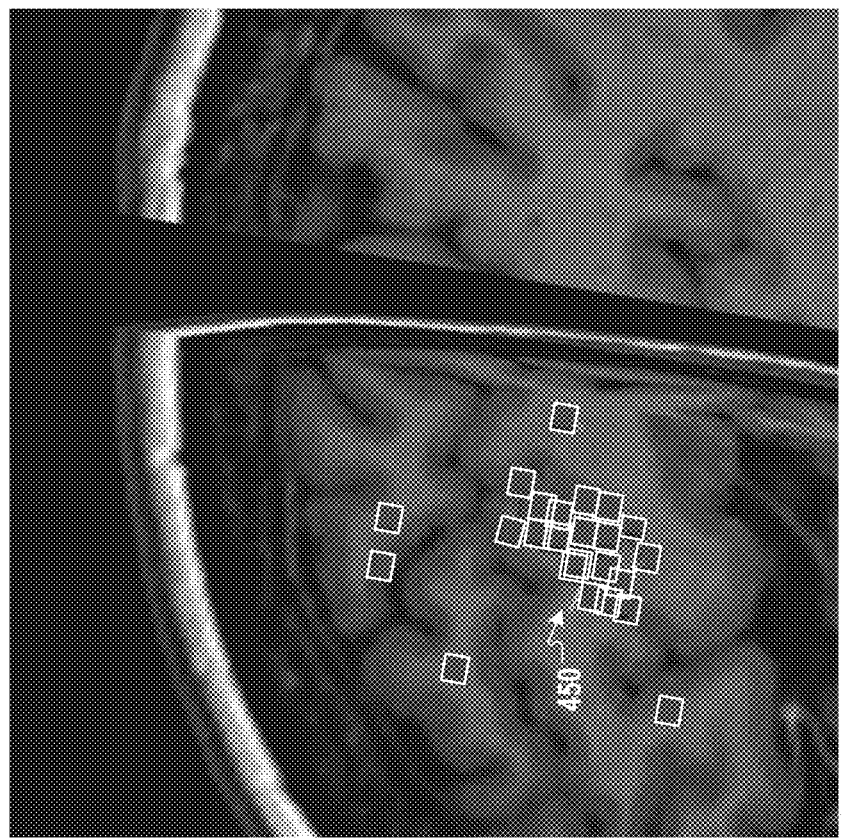
FIG. 4B illustrates an example updated connectivity matrix and corresponding updated brain image data.
Figure 4B:
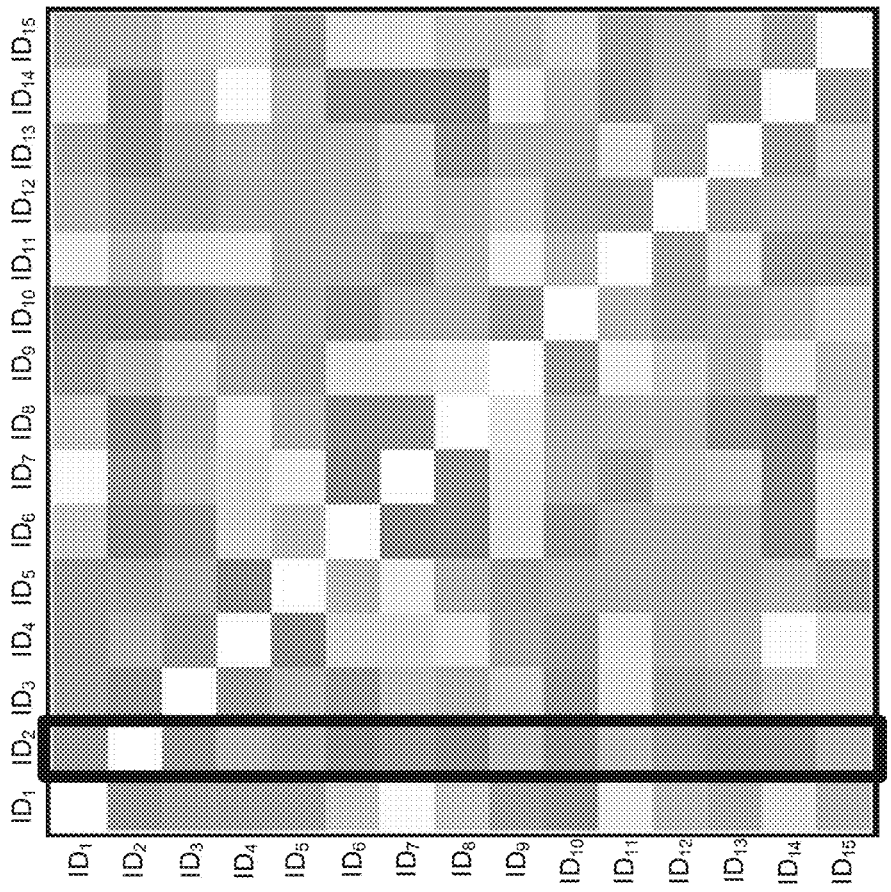

FIG. 4B illustrates an example updated connectivity matrix 430 and corresponding updated brain image data 440. The updated connectivity matrix 430 is an updated version of the connectivity matrix 410, after the user has selected a particular column of the connectivity matrix 410 (in this case, the second column). That is, after the user selects the second column of the connectivity matrix 410, the graphical user interface can visually identify the selected column, displaying the updated connectivity matrix 430. The graphical user interface can visually identify the selected column in any way, e.g, by outlining the selected column (as depicted in FIG. 4B), highlighting the selected column, dimming the unselected columns, etc.

Although a column of the connectivity matrix 410 is selected in FIG. 4B, it is to be understood that the following description can also apply to rows of the connectivity matrix 410. Similarly, although a single column of the connectivity matrix 410 is selected in FIG. 4B, it is to be understood that the following description can also apply to any number of selected columns of the connectivity matrix 410.

Each column of the updated connectivity matrix 430 corresponds to a particular parcellation of the brain of the patient, and can have a corresponding parcellation identification $ID_N$. The parcellation identifications, depicted in FIG. 4B, may or may not be displayed for the user by the graphical user interface. The user can select the desired column in any appropriate way, e.g., by clicking on the corresponding parcellation identification number, or by clicking on any element of the column.

The graphical user interface can determine the parcellation identification of the column selected by the user (in this case, $ID_2$) and send the parcellation identification to a target generation system, e.g., the target generation system 240 depicted in FIG. 2. The target generation system can also obtain brain atlas data defining the parcellations of the human brain. The target generation system can then determine, according to the parcellation identification, a subset of the brain atlas data that characterizes the parcellation corresponding to the selected column of the updated connectivity matrix 430. The target generation system can provide the subset of the brain atlas data to the graphical user interface.

The graphical user interface can use the subset of the brain atlas data to generate the updated brain image data 440. The updated brain image data 440 is an updated version of the brain image data 420, after the user has selected the second column of the connectivity matrix 410. The updated brain image data 440 depicts the portion of the brain image data 410 that corresponds to the parcellation corresponding to the column of the connectivity matrix 410 selected by the user.

In particular, the updated brain image data 440 can visually identify the parcellation corresponding to the selected column, as defined by the obtained subset of the brain atlas data. For example, the brain atlas data can include multiple voxels each assigned to a particular parcellation. In this case, the updated brain image data 440 can include a depiction of the voxels 450 in the brain atlas data that are assigned to the parcellation corresponding to the selected column. The location of the depiction of the voxels 450 in the updated brain image data 440 is defined by the obtained subset of the brain atlas data.

In some implementations, the user can select multiple different columns of the connectivity matrix 410, causing the graphical user interface to visually identify the multiple selected columns and display an updated connectivity matrix. The graphical user interface can also generate updated brain image data that depicts the different portions of the brain image data 410 that correspond to the respective parcellations corresponding to the multiple different columns of the connectivity matrix 410 selected by the user. In some such implementations, the graphical user interface can visually identify the different parcellations, e.g., using different colors where each color corresponds to a respective parcellation.

Figure 5:
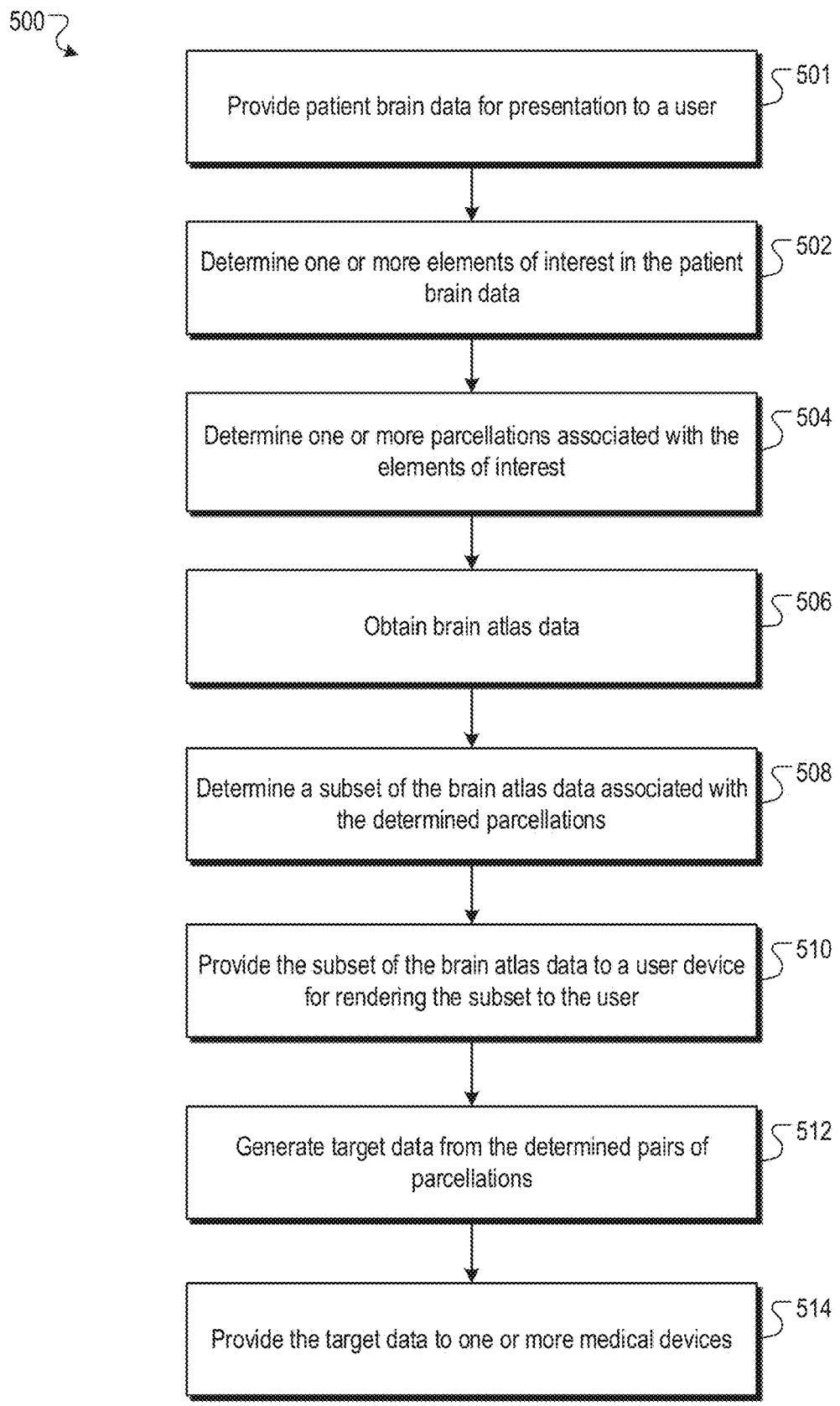
FIG. 5 is a flowchart of an example process for determining target data from patient brain data.

FIG. 5 is a flowchart of an example process 500 for determining target data from patient brain data. The process 500 can be implemented by one or more computer programs installed on one or more computers and programmed in accordance with this specification. For example, the process 500 can be performed by the computer server module depicted in FIG. 1A. For convenience, the process 500 will be described as being performed by a system of one or more computers.

The system provides patient brain data for presentation to a user (step 501). The patient brain data can include tractography data and/or connectivity data characterizing the brain of a patient.

The connectivity data can characterize, for each pair of parcellations including a first parcellation and a second parcellation from a set of multiple parcellations, a degree of correlation between the brain activity of the first parcellation and the brain activity of the second parcellation in the brain of a patient. In some implementations, the connectivity data specifies a connectivity matrix and each position in the connectivity matrix characterizes a pair of parcellations.

In some implementations, the system can identify one or more pairs of parcellations from the set of parcellations for which the correlation between brain activity of the first parcellation and the second parcellation in the brain of the patient specified in the connectivity data is outside of a normal range of correlations. The system can then provide data characterizing the one or more identified pairs of parcellations for display to the user on a graphical interface.

The system determines one or more elements of interest in the patient brain data (step 502). For example, the system can receive a selection from the user of one or more positions in a connectivity matrix characterizing the correlation between pairs of parcellations in the brain of the patient. As a particular example, the system can receive a selection of a column or a row of a connectivity matrix.

The system determines one or more parcellations associated with the elements of interest (step 504). For example, each element of interest can include an identification of a particular parcellation.

The system obtains brain atlas data (step 506).

The system determines a subset of the brain atlas data associated with the determined parcellations (step 508).

The system provides the subset of the brain atlas data to a user device for rendering the subset to the user (step 510).

The system processes the determined pair of parcellations to generate target data for a treatment of the patient (step 512).

The system provides the target data to one or more medical devices for executing the treatment of the patient (step 514).

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program which may also be referred to or described as a program, software, a software application, an app, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and pointing device, e.g, a mouse, trackball, or a presence sensitive display or other surface by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

In addition to the embodiments described above, the following embodiments are also innovative:

Embodiment 1 is a method comprising:

providing connectivity data for presentation to a user, the connectivity data characterizing, for each pair of parcellations comprising a first parcellation and a second parcellation from a plurality of parcellations, a degree of correlation between the brain activity of the first parcellation and the brain activity of the second parcellation in the brain of a patient;

determining one or more elements of interest in the connectivity data;

determining one or more parcellations associated with elements of interest in the connectivity data;

obtaining brain atlas data;

determining a subset of the brain atlas data associated with the determined parcellations; and providing the subset of the brain atlas data to a user device for rendering the subset to the user.

Embodiment 2 is the method of embodiment 1, wherein providing connectivity data for presentation to a user further comprises:

identifying one or more pairs of parcellations from the plurality of parcellations for which the correlation between brain activity of the first parcellation and the second parcellation in the brain of the patient specified in the connectivity data is outside of a normal range of correlations corresponding to the pair of parcellations; and providing data characterizing the one or more identified pairs of parcellations for display to a user on a graphical interface.

Embodiment 3 is the method of any one of embodiments 1 or 2, wherein the connectivity data specifies a connectivity matrix and each position in the connectivity matrix characterizes a pair of parcellations.

Embodiment 4 is the method of embodiment 3, wherein determining one or more elements of interest in the connectivity matrix comprises receiving a selection from a user of one or more positions in the connectivity matrix.

Embodiment 5 is the method of embodiment 4, wherein receiving a selection of one or more positions in the connectivity matrix comprises receiving one or more of: a selection of a column of the connectivity matrix or a selection of a row of the connectivity matrix.

Embodiment 6 is the method of any one of embodiments 1-5, further comprising processing the determined pairs of parcellations to generate target data for a treatment of the patient.

Embodiment 7 is the method of embodiment 6, further comprising providing the target data to one or more medical devices for executing the treatment of the patient.

Embodiment 8 is a system comprising one or more computers and one or more storage devices storing instructions that are operable, when executed by the one or more computers, to cause the one or more computers to perform the method of any one of embodiments 1-7.

Embodiment 9 is a computer storage medium encoded with a computer program, the program comprising instructions that are operable, when executed by data processing apparatus, to cause the data processing apparatus to perform the method of any one of embodiments 1-7.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain some cases, multitasking and parallel processing may be advantageous.

What is claimed is:

1. A method comprising:
   obtaining connectivity data characterizing, for each pair of parcellations comprising a first parcellation and a second parcellation from a plurality of parcellations, a degree of correlation between brain activity of the first parcellation and brain activity of the second parcellation in a brain of a patient;
   identifying one or more pairs of parcellations from the plurality of pairs of parcellations for which the degree of correlation specified in the connectivity data is outside of a normal range of correlations corresponding to the pair of parcellations;
   providing data characterizing the one or more identified pairs of parcellations for presentation to a user;
   determining one or more elements of interest in the connectivity data;
   determining one or more parcellations associated with respective elements of interest in the connectivity data;
   obtaining brain atlas data;
   determining a subset of the brain atlas data associated with the determined parcellations; and
   providing the subset of the brain atlas data for presentation to the user.

2. The method of claim 1, wherein the connectivity data specifies a connectivity matrix and each position in the connectivity matrix characterizes a pair of parcellations.

3. The method of claim 2, wherein determining one or more elements of interest in the connectivity matrix comprises receiving, from the user, a selection of one or more positions in the connectivity matrix.

4. The method of claim 3, wherein receiving a selection of one or more positions in the connectivity matrix comprises receiving one or more of: a selection of a column of the connectivity matrix or a selection of a row of the connectivity matrix.

5. The method of claim 1, further comprising processing the determined subset of the brain atlas data to generate target data for a treatment of the patient.

6. The method of claim 5, further comprising providing the target data to one or more medical devices for executing the treatment of the patient.

7. The method of claim 1, wherein:
   the normal range of correlations corresponding to a particular pair parcellations is defined according to i) an average correlation between brain activity of the particular pair of parcellations and ii) a degree of variation of correlations between brain activity of the particular pair of parcellations; and
   the average correlation and the degree of variation of correlations having been determined using brain data corresponding to a plurality of second patients.

8. The method of claim 4, wherein providing the subset of the brain atlas data for presentation to the user comprises:
   providing data representing an interface to a user device for displaying the interface to the user, wherein the interface comprises i) a visual indication of selected column or row of the connectivity matrix, and ii) a visual representation of the subset of the brain atlas data.

9. A system comprising one or more computers and one or more storage devices storing instructions that are operable, when executed by the one or more computers, to cause the one or more computers to perform operations comprising:
   obtaining connectivity data characterizing, for each pair of parcellations comprising a first parcellation and a second parcellation from a plurality of parcellations, a degree of correlation between brain activity of the first parcellation and brain activity of the second parcellation in a brain of a patient;

identifying one or more pairs of parcellations from the plurality of pairs of parcellations for which the degree of correlation specified in the connectivity data is outside of a normal range of correlations corresponding to the pair of parcellations;

providing data characterizing the one or more identified pairs of parcellations for presentation to a user;

determining one or more elements of interest in the connectivity data;

determining one or more parcellations associated with respective elements of interest in the connectivity data;

obtaining brain atlas data;

determining a subset of the brain atlas data associated with the determined parcellations; and providing the subset of the brain atlas data for presentation to the user.

10. The system of claim 9, wherein the connectivity data specifies a connectivity matrix and each position in the connectivity matrix characterizes a pair of parcellations.

11. The system of claim 10, wherein determining one or more elements of interest in the connectivity matrix comprises receiving, from the user, a selection of one or more positions in the connectivity matrix.

12. The system of claim 11, wherein receiving a selection of one or more positions in the connectivity matrix comprises receiving one or more of: a selection of a column of the connectivity matrix or a selection of a row of the connectivity matrix.

13. The system of claim 9, wherein the operations further comprise processing the determined subset of the brain atlas data to generate target data for a treatment of the patient.

14. The system of claim 13, wherein the operations further comprise providing the target data to one or more medical devices for executing the treatment of the patient.

15. One or more non-transitory storage media storing instructions that when executed by one or more computers cause the one or more computers to perform operations comprising:

obtaining connectivity data characterizing, for each pair of parcellations comprising a first parcellation and a second parcellation from a plurality of parcellations, a degree of correlation between brain activity of the first parcellation and brain activity of the second parcellation in a brain of a patient;

identifying one or more pairs of parcellations from the plurality of pairs of parcellations for which the degree of correlation specified in the connectivity data is outside of a normal range of correlations corresponding to the pair of parcellations;

providing data characterizing the one or more identified pairs of parcellations for presentation to a user;

determining one or more elements of interest in the connectivity data;

determining one or more parcellations associated with respective elements of interest in the connectivity data;

obtaining brain atlas data;

determining a subset of the brain atlas data associated with the determined parcellations; and providing the subset of the brain atlas data for presentation to the user.

16. The non-transitory storage media of claim 15, wherein the connectivity data specifies a connectivity matrix and each position in the connectivity matrix characterizes a pair of parcellations.

17. The non-transitory storage media of claim 16, wherein determining one or more elements of interest in the connectivity matrix comprises receiving, from the user, a selection of one or more positions in the connectivity matrix.

18. The non-transitory storage media of claim 17, wherein receiving a selection of one or more positions in the connectivity matrix comprises receiving one or more of: a selection of a column of the connectivity matrix or a selection of a row of the connectivity matrix.

19. The non-transitory storage media of claim 15, wherein the operations further comprise processing the determined subset of the brain atlas data to generate target data for a treatment of the patient.

20. The non-transitory storage media of claim 19, wherein the operations further comprise providing the target data to one or more medical devices for executing the treatment of the patient.

* * * * *